(12) United States Patent
Clarke

(10) Patent No.: US 10,390,560 B2
(45) Date of Patent: Aug. 27, 2019

(54) FLAVOUR STICK

(75) Inventor: Paul F. Clarke, Northumberland (GB)

(73) Assignee: Filtrona Filter Products Development Co. Pte. Ltd., Novena Square (SG)

( * ) Notice: Subject to any disclaimer, the term of this patent is extended or adjusted under 35 U.S.C. 154(b) by 884 days.

(21) Appl. No.: 13/996,626

(22) PCT Filed: Dec. 19, 2011

(86) PCT No.: PCT/GB2011/001737
§ 371 (c)(1),
(2), (4) Date: Aug. 29, 2013

(87) PCT Pub. No.: WO2012/085499
PCT Pub. Date: Jun. 28, 2012

(65) Prior Publication Data
US 2013/0327345 A1    Dec. 12, 2013

(30) Foreign Application Priority Data

Dec. 21, 2010 (GB) .................................. 1021827.9

(51) Int. Cl.
A24F 15/18 (2006.01)
A24C 5/60 (2006.01)
A61L 9/04 (2006.01)
A61L 9/12 (2006.01)
B65D 85/10 (2006.01)

(52) U.S. Cl.
CPC ............... *A24F 15/18* (2013.01); *A24C 5/60* (2013.01); *A61L 9/04* (2013.01); *A61L 9/042* (2013.01); *A61L 9/12* (2013.01); *B65D 85/1081* (2013.01)

(58) Field of Classification Search
CPC .............................. A24D 1/02; B65D 85/1081
See application file for complete search history.

(56) References Cited

U.S. PATENT DOCUMENTS

| 1,972,118 | A |   | 1/1932  | McDill |
|-----------|---|---|---------|--------|
| 2,007,632 | A | * | 7/1935  | Blank .................. A24B 15/282 |
|           |   |   |         | 131/274 |
| 2,169,055 | A |   | 8/1939  | Overshiner |
| 4,481,954 | A | * | 11/1984 | Luke ....................... A24D 1/02 |
|           |   |   |         | 131/360 |
| 4,662,384 | A |   | 5/1987  | Green |
| 5,938,018 | A |   | 8/1999  | Keaveney et al. |
| 6,041,790 | A | * | 3/2000  | Smith ................... A24B 15/16 |
|           |   |   |         | 131/360 |

(Continued)

FOREIGN PATENT DOCUMENTS

DE    10 2006 029 092 A1    12/2007
EP       0 531 075 A1        3/1993

(Continued)

OTHER PUBLICATIONS

PCT/ISA/210 dated Mar. 21, 2012 (7 pages).

(Continued)

*Primary Examiner* — Eric Yaary
(74) *Attorney, Agent, or Firm* — Flynn Thiel, P.C.

(57) ABSTRACT

An insert comprising a substrate and a flavoring agent, wherein the flavoring agent is present in an amount from 50 to 500 mg per $cm^3$ volume of the substrate. The insert is used for introducing a flavor, or increasing the level of flavor applied, to one or more smoking articles in a package of smoking articles, by enclosing the insert within such a package.

18 Claims, 1 Drawing Sheet

(56) References Cited

U.S. PATENT DOCUMENTS

| | | | |
|---|---|---|---|
| 6,417,156 B1* | 7/2002 | Smith | A61L 9/12 510/515 |
| 2002/0127189 A1 | 9/2002 | Myers et al. | |
| 2008/0017206 A1* | 1/2008 | Becker | A23L 1/22025 131/276 |
| 2009/0288669 A1* | 11/2009 | Hutchens | A24D 3/0212 131/274 |
| 2010/0236561 A1* | 9/2010 | Barnes | A24D 3/0216 131/58 |
| 2011/0139669 A1 | 6/2011 | Huppert et al. | |
| 2011/0232659 A1* | 9/2011 | Ercelebi | A24D 3/0216 131/280 |
| 2011/0240046 A1* | 10/2011 | Hasegawa | A24D 3/04 131/275 |
| 2012/0012479 A1* | 1/2012 | Hodges | A24C 5/608 206/265 |

FOREIGN PATENT DOCUMENTS

| | | | |
|---|---|---|---|
| EP | 1 803 662 A1 | 7/2007 | |
| FR | 2 584 273 | 1/1987 | |
| GB | 2467971 A | 8/2010 | |
| JP | WO 2010079793 A1 * | 7/2010 | ............... A24D 3/04 |
| WO | WO 98/44961 | 10/1998 | |
| WO | WO 2005/070241 A2 | 8/2005 | |
| WO | WO 2007/071990 A1 | 6/2007 | |
| WO | WO 2007/123046 A1 | 11/2007 | |
| WO | WO 2008/148702 A1 | 12/2008 | |
| WO | WO 2009092823 A1 * | 7/2009 | ......... B65D 85/1081 |
| WO | WO 2009135729 A1 * | 11/2009 | ........... A24F 47/002 |
| WO | WO 2010/097252 A1 | 9/2010 | |

OTHER PUBLICATIONS

PCT/ISA/237 dated Mar. 21, 2012 (8 pages).
Examination Report of European Patent Office issued in Application No. 11 808 256.9 dated Sep. 30, 2015 (5 pages).
Search Report from the UKIPO for Application No. GB1021827.9 dated Feb. 15, 2011 (4 pages).
Examination Report issued in European Application No. 11 808 256.9 dated Feb. 6, 2017 (6 pages).

* cited by examiner

FLAVOUR STICK

The present invention is related to smoking articles such as cigarettes, in particular smoking articles which include flavouring agents.

Menthol flavoured cigarettes are well known in the tobacco industry and are popular with many smokers. There are numerous ways in which menthol can be applied to cigarettes by the cigarette manufacturer. It can be applied to tobacco at the tobacco processing stage, it can be applied to the cigarette paper or to the filter during cigarette manufacture or it can be applied to the inner foil liner of the cigarette pack prior to forming and sealing the cigarette pack. Due to the volatile nature of menthol, the flavour will be evenly distributed throughout the cigarette during storage regardless of where the menthol was originally applied (assuming that storage takes place in a sealed container).

Two limitations with menthol cigarettes are that the smoker has little discretion over whether his preferred brand is available as a menthol cigarette. Further, the smoker has no control over the level of menthol applied to the cigarette (this is pre-determined by the cigarette manufacturer). The present invention overcomes both these disadvantages.

According to the present invention in a first aspect there is provided an insert (e.g. a flavouring insert, e.g. an insert for a package) comprising a substrate (e.g. a fibrous substrate); and a flavouring agent (e.g. volatile flavouring agent). The insert is a discrete insert, which is separate and distinct from the package. Preferably the flavouring agent is located on and/or in the substrate. Preferably the substrate is not a smoking article such as a cigarette. Preferable the substrate is not a package liner (e.g. a package liner which is integral to the package) such as a foil.

Herein the term discrete insert means that the insert (flavouring insert) is a separate and distinct entity to the package (e.g. it may be sold separately for use with a package).

The insert may be for enclosure within a package of smoking articles (e.g. cigarettes) or a package of tobacco.

The flavouring agent may be a flavouring agent known or suitable for use in a smoking article such as a cigarette, for example menthol, spearmint, clove etc. Preferably the flavouring agent is or comprises menthol. The insert may comprise more than one flavouring agent (and may provide blends of different flavours, which may or may not include menthol).

Preferably the flavouring agent is present in the amount from 50 to 500 mg per $cm^3$ volume of the substrate, for example 100 to 475 mg per $cm^3$ volume of the substrate, for example 250 to 450 mg per $cm^3$ volume of the substrate, for example 380 to 420 mg per $cm^3$ volume of the substrate. In an example, the flavouring agent comprises menthol and the flavouring agent is present in the amount from 300 to 500 mg per $cm^3$ volume of the substrate. In another example, the flavouring agent comprises cloves (e.g. oil of cloves) and the flavouring agent is present in the amount from 100 to 400 mg per $cm^3$ volume of the substrate.

The insert (e.g. flavouring insert) may further comprise a wrapper (or membrane) for the substrate. Preferably the wrapper or membrane is permeable to the flavouring agent.

The insert (e.g. flavouring insert) may further comprise an adhesive portion (e.g. a self adhesive portion). The adhesive portion may be used to fix the insert within the package (e.g. within the lid of the package).

The substrate may comprise a fibrous material, for example a natural or synthetic fibrous material. Preferably, the substrate comprises a cellulose acetate, e.g. a tow of filamentary cellulose acetate. In one example, the substrate comprises a cylindrical rod comprising (e.g. cellulose acetate) filaments (e.g. which have been gathered together and condensed into rod form). The insert may optionally include a wrapper (or membrane) for the substrate. Preferably the wrapper or membrane is permeable to the flavouring agent.

The wrapper may be a naturally permeable material or a non-permeable material which has been treated (e.g. perforated, e.g. perforated mechanically) to provide permeability. The wrapper or membrane may be, e.g. a porous plug wrap paper. The membrane may be omitted (e.g. as in 'non-wrapped acetate' cigarette filter rods). The substrate may be of similar dimensions to a cigarette (e.g. 70 to 120 mm, e.g. 84 mm, long and about 14 to 24.5 mm, e.g. about 24.5 mm, in circumference).

In another example, the substrate comprises a sheet of material, e.g. a pad or wad comprising a sheet material. The larger surface area of a sheet (in comparison to a rod form of similar weight) may enhance the rate of flavour, e.g. menthol, transfer to cigarettes in the pack into which it is inserted. The sheet of material may comprise a non-woven material for example a non-woven web made from a natural and/or a synthetic fibre. The thickness of the wad may be significantly smaller than its length or width, which may make it easier for the smoker to insert the pad into a full pack of cigarettes. The pad can be of any size smaller than the length and width of the pack into which it is inserted. The insert may further comprise a wrapper (or membrane) for the sheet material. In a preferred embodiment the sheet of material (pad or wad) is dimensioned (sized) such that it fits in the lid portion of the package, e.g. dimensioned to fit in the hinged lid of a hard pack of cigarettes without preventing the lid from closing (such hard packs and lids are well known). The insert may, for example, be of length 30 to 60 mm (e.g. 50 to 55 mm), width 10 to 20 mm, and depth 0.01 to 2 mm. In examples of this embodiment the insert (e.g. flavouring insert) may further comprise an adhesive portion (e.g. a self adhesive portion), to fix the insert within the lid of the package. In examples of this embodiment the insert (discrete insert) may be a sheet, e.g. a mentholated sheet.

The positioning of the insert in the lid of the package means that the filter ends of the cigarettes are evenly exposed to flavouring agent (e.g. menthol) on the insert, which may provide a more even flavouring (over all cigarettes in the package).

Thus, the present invention provides a flavoured (e.g. menthol flavoured) insert (e.g. pad or stick or other similar object) which the smoker can introduce to a pack of cigarettes (preferably, but not necessarily a non-mentholated brand of cigarettes) and leave in the pack for a suitable period of time to allow menthol to migrate from the pad to the cigarettes such that the cigarettes become mentholated. It is possible to apply different levels of menthol to the pad or stick and the smoker can adjust the level of menthol present in the cigarette by selecting a pad with an appropriate level of menthol addition and by the length of time the pad is left in the pack. Following introduction of the insert into the pack, the pack (and insert) may be heated (in an oven) to accelerate the transfer of flavouring agent from the insert to the cigarettes. It will be appreciated that more than one insert may be added to a pack e.g. to increase flavouring, if desired.

According to the present invention in a further aspect there is provided a method of introducing flavour, or increasing the level of flavour applied, to one or more smoking articles in a package of smoking articles, comprising a step of enclosing within the package at least one discrete insert comprising a substrate (e.g. a fibrous substrate); and a flavouring agent (e.g. volatile flavouring agent). The (or each) discrete insert may be any insert according to the invention as described herein. The (or each) discrete insert may be stored in the package (with the smoking articles for a period of time (e.g. 0.5 to 7 days). The (or each) discrete insert may be located in the package lid. It will be appreciated that if more than one discrete insert is used, the inserts may be the same or different (in terms of size, shape, loading etc.). The method may comprise a further step of heating the package (with discrete insert(s) and smoking article(s) therein. The heating may be to a temperature above 25 degrees C. The heating may be for a period of 1 to 10 minutes.

The heating may take place in an oven. The heating will accelerate the transfer of flavouring agent from the insert to the cigarettes.

The applicants have found that including a flavouring agent in an amount from 50 to 500 mg per $cm^3$ volume of the substrate, for example 100 to 475 mg per $cm^3$ volume of the substrate, for example 250 to 450 mg per $cm^3$ volume of the substrate, for example 380 to 420 mg per $cm^3$ volume of the substrate, may provide effective flavouring of the smoking articles in the package.

The substrate (e.g. pad or stick) may be loaded with flavouring agent (e.g. menthol) by dipping it or coating it with molten flavouring agent (e.g. menthol). In an alternative, the substrate (pad or stick) may be dipped or sprayed with flavouring agent (e.g. menthol) that has been dissolved in a suitable solvent (such as propylene glycol). The amount of flavouring agent (e.g. menthol) on the pad can be controlled, e.g. by selecting the size of the pad and/or the concentration of loading of the flavouring agent.

The insert (substrate) may also be used to mentholate a pouch (or other container) of tobacco (e.g. cut tobacco) for smokers of Roll-Your-Own or Make-Your-Own smoking products (cigarettes etc.).

The inserts are preferably packed in a sealed container or enclosure to minimize loss of menthol on storage prior to use. It is envisaged that the smoker would open the sealed enclosure shortly before use. An insert may contain sufficient menthol to mentholate a single pack of cigarettes or it may contain sufficient menthol to be used on multiple, successive packs of cigarettes. An insert may further include a barrier region (comprising a barrier material which is impermeable to the flavouring agent). The barrier region may provide some protection when handling to minimize potential contact between the smokers fingers and the flavour agent bearing (mentholated) fibrous material.

The present invention is now illustrated with reference to the following examples and the attached drawings in which.

Figure 1:
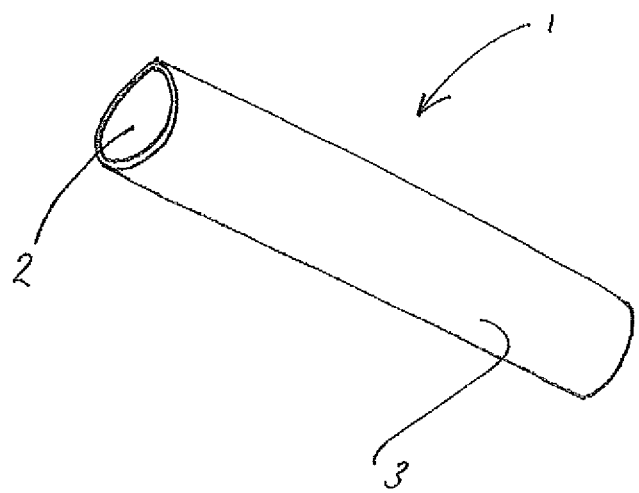
FIG. 1 illustrates a first example of an insert according to the invention.

FIG. 1 shows a first example of a flavouring insert (a discrete flavouring insert) according to the invention. The insert 1 comprises a substrate in the form of a cylinder 2 of cellulose acetate which has been gathered together and condensed into rod form by methods well known in the art. The cylinder 2 is of circumference approximately 24.5 mm and length approximately 84 mm (i.e. approximately the same dimensions of a normal sized filter cigarette). The cylinder 2 is surrounded by a wrapper 3 of porous plug wrap paper, which is applied around the cellulose acetate tow as, or shortly after, it is condensed into rod form, again by methods well known in the art. The cylinder 2 of cellulose acetate tow bears 405 mg of menthol flavouring agent per $cm^3$ of volume of the cylinder. This flavouring agent is preferably applied to the cellulose acetate tow prior to wrapping by methods known in the art: for example, molten menthol may be applied to the cellulose acetate tow before being gathered together and condensed into rod form, or may be dipped in molten menthol while in rod form prior to being wrapped. Alternatively, the rod form may be dipped in molten menthol after the rod has been formed and wrapped.

The insert 1 (comprising cylinder 2 including a flavouring agent on the cylinder 2) may be used to flavour cigarettes. Following production of the insert 1, the insert 1 is sealed (for example vacuum packed) in a substantially flavour-impermeable membrane (not shown), which minimise loss of menthol on storage prior to use. The user will remove the membrane and place the insert 1 into a packet of cigarettes (e.g. first removing one cigarette to provide a space). The insert of FIG. 1 includes sufficient menthol to mentholate (i.e. flavour with menthol) a single pack of twenty cigarettes following storage of the insert with the cigarettes for a period of approximately one to three days.

It will be appreciated that the insert may be used with a package of already mentholated cigarettes (in which case the menthol flavour will be stronger) or an unmentholated packet of cigarettes to provide some menthol flavouring.

It will also be appreciated that following introduction of the insert into the pack, the pack with insert may be heated (in an oven) for e.g. 5 minutes to accelerate the transfer of flavouring agent from the insert to the cigarettes.

Figure 2:
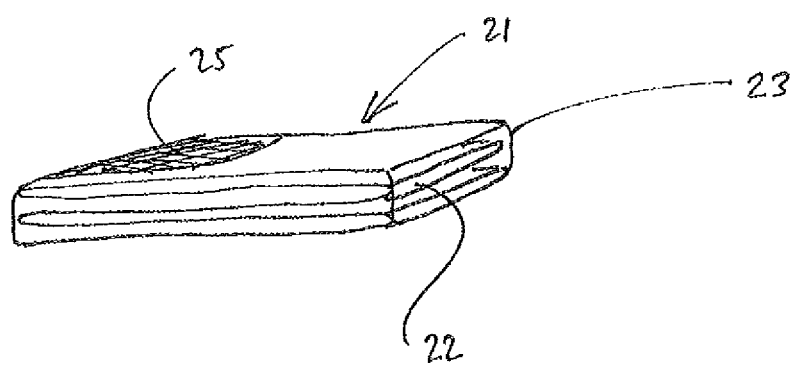
FIG. 2 illustrates a further example of an insert according to the invention.

FIG. 2 shows a further example of a flavouring insert (discrete insert) according to the invention. The insert 21 comprises a substrate in the form of a sheet 22 formed of a non-woven material made by methods well known in the art. The sheet 22 is optionally laminated to a wrapper 23 of porous lightweight nonwoven material. Sheet 22 bears 405 mg of menthol flavouring agent per $cm^3$ of volume of the sheet. This flavouring agent may be applied to the nonwoven sheet prior to laminating by methods known in the art, e.g. by applying molten menthol to the sheet. Flavouring insert 22 further comprises a barrier 25 of polyethylene at one end which provides some protection when handling to minimize potential contact between the smokers fingers and the flavouring agent bearing (mentholated) non-woven material.

The insert of FIG. 2 may be of length 57 mm, width 19 mm, and depth 0.1 mm so that it may be placed within the lid of a conventional hard packet of cigarettes such that the lid may be closed (or substantially fully closed) on the cigarettes with the insert located therein. The positioning of the insert in the lid of the package means that the filter ends of the cigarettes are evenly exposed to menthol on the insert; this may provide a more even flavouring effect.

EXAMPLE 1

Thin fibrous strips were loaded with menthol through dipping in molten menthol and inserted into freshly opened packs of a commercial non-menthol cigarette brand. Strips of two different sizes were used—a larger strip of 84×10×1 mm containing around 340 mg and a smaller strip of 42×10×1 mm containing about 170 mg menthol per strip. A small tab of plastic sheet was adhered to each strip to facilitate handling and minimize direct contact with the mentholated strip. A strip of each size was added to each of 5 cigarette packs and every 24 hours a different pack was sampled and ten cigarettes removed at random for menthol loading testing under ISO smoking conditions. The results are given in the table below.

| Cigarette Age | Mean Menthol Yield (mg/cig) | |
| --- | --- | --- |
| (Days) | Larger Strip | Smaller Strip |
| 1 | 1.80 | 0.79 |
| 2 | 2.27 | 1.04 |
| 3 | 2.81 | 1.65 |
| 4 | 4.26 | 2.29 |
| 7 | 4.78 | 3.00 |

It can be seen that menthol does transfer readily and rapidly from the strips to the cigarettes.

EXAMPLE 2

Menthol Inserts

Two insert types were tested. The rod insert included a cylindrical rod of plasticised cellulose acetate of 15.7 mm circumference and 84 mm length wrapped in a perforated film wrap (similar construction to the embodiment of FIG. 1, with perforated film rather than plugwrap). The flat pad insert included an unwrapped flat pad of plasticised cellulose acetate of 20 mm width, 3 mm thickness and 84 mm length. Inserts were pre loaded with 100 mg, 200 mg and 300 mg menthol and then inserted in cigarette packs which were resealed. After insertion of the inserts the cigarettes were sampled after 24 and 48 hours and the menthol yield measured for the cigarettes nearest to the insert. The results are given in the table below.

| Time Pack Sealed Hrs | Menthol mg/Insert | Menthol Yield mg/cig |
| --- | --- | --- |
| Rod Insert | | |
| 24 | 100 | 0.19 |
|  | 200 | 0.29 |
|  | 300 | 0.99 |
| 48 | 100 | 0.31 |
|  | 200 | 0.42 |
|  | 300 | 1.15 |
| Flat Pad Insert | | |
| 24 | 100 | 0.25 |
|  | 200 | 0.37 |
|  | 300 | 0.46 |
| 48 | 100 | 0.25 |
|  | 200 | 0.54 |
|  | 300 | 0.62 |

It can be seen that menthol does transfer readily and rapidly from the inserts to the cigarettes.

The invention claimed is:

1. A tobacco product package comprising:
a lid hinged to a main body; and
a flavouring insert comprising a substrate and a flavouring agent, wherein the substrate comprises a sheet of cellulose acetate material, wherein the flavouring agent comprises menthol or clove, and wherein the menthol or clove is present in an amount from 50 to 500 mg per cm$^3$ volume of the substrate;
wherein the flavouring insert is enclosed within the lid.

2. The tobacco product package according to claim 1 wherein the flavouring agent is present in an amount from 100 to 475 mg per cm$^3$ volume of the substrate.

3. The tobacco product package according to claim 1, wherein the substrate is not a smoking article or a package liner.

4. The tobacco product package according to claim 1 wherein the flavouring agent is or comprises menthol and the menthol is present in an amount from 300 to 500 mg per cm$^3$ volume of the substrate.

5. The tobacco product package according to claim 1 wherein the flavouring agent is or comprises clove and the clove is present in an amount from 100 to 400 mg per cm$^3$ volume of the substrate.

6. The tobacco product package according to claim 1 wherein the substrate comprises a fibrous material.

7. The tobacco product package according to claim 1 further comprising a wrapper or membrane for the substrate.

8. The tobacco product package according to claim 1 further comprising a barrier region.

9. The tobacco product package according to claim 1 further comprising an adhesive portion.

10. A method of introducing flavour, or increasing a level of flavour applied, to at least one smoking article, the method comprising:
providing a package including a lid hinged to a main body; and
enclosing within the lid a discrete insert comprising a substrate and a flavouring agent, wherein the substrate comprises a sheet of cellulose acetate material, wherein the flavouring agent comprises menthol or clove, and wherein the menthol or clove is present in an amount from 50 to 500 mg per cm$^3$ volume of the substrate.

11. The method according to claim 10 comprising a further step of heating the package with the discrete insert and the at least one smoking article therein to a temperature above 25 degrees C.

12. The tobacco product package according to claim 2 wherein the flavouring agent is present in an amount from 250 to 450 mg per cm$^3$ volume of the substrate.

13. The tobacco product package according to claim 2 wherein the flavouring agent is present in an amount from 380 to 420 mg per cm$^3$ volume of the substrate.

14. A tobacco product flavouring insert comprising a substrate, a flavouring agent, and a barrier region; wherein the substrate comprises a cylindrical rod of cellulose acetate, wherein the barrier region comprises barrier material which is impermeable to the flavouring agent, wherein the flavouring agent comprises menthol or clove, and wherein the menthol or clove is present in an amount from 50 to 500 mg per cm$^3$ volume of the substrate.

15. The tobacco product flavouring insert according to claim 14 wherein the cylindrical rod has a length of 84 mm and a circumference of 24.5 mm.

16. The tobacco product flavouring insert according to claim 14 wherein the cylindrical rod has a length of 70 to 120 mm and a circumference of about 14 to about 24.5 mm.

17. The tobacco product package according to claim 1, wherein the lid is smaller than the main body.

18. The method according to claim 10, wherein the lid is smaller than the main body.

* * * * *